United States Patent
Krantz et al.

(10) Patent No.: US 7,343,190 B2
(45) Date of Patent: Mar. 11, 2008

(54) SYSTEM AND METHOD FOR ASSESSING FETAL ABNORMALITY BASED ON LANDMARKS

(75) Inventors: David A. Krantz, Bayside, NY (US); Francesco Orlandi, Palermo (IT); Vincent James Macri, Oyster Bay, NY (US)

(73) Assignee: NTD Laboratories, Inc., Huntington Station, NY (US)

( * ) Notice: Subject to any disclaimer, the term of this patent is extended or adjusted under 35 U.S.C. 154(b) by 424 days.

(21) Appl. No.: 10/900,292

(22) Filed: Jul. 28, 2004

(65) Prior Publication Data

US 2005/0245825 A1 Nov. 3, 2005

Related U.S. Application Data

(60) Provisional application No. 60/493,442, filed on Aug. 8, 2003, provisional application No. 60/490,540, filed on Jul. 29, 2003.

(51) Int. Cl.
*A61B 5/04* (2006.01)
*A61B 8/00* (2006.01)

(52) U.S. Cl. .................... 600/407; 600/443; 382/128

(58) Field of Classification Search ............ 600/407, 600/409, 437, 443–447, 458; 128/916; 382/190, 382/195, 199, 203–204, 207, 294
See application file for complete search history.

(56) References Cited

U.S. PATENT DOCUMENTS

| | | | |
|---|---|---|---|
| 5,235,981 A | 8/1993 | Hascoet et al. | |
| 5,252,489 A | 10/1993 | Macri | |
| 5,588,435 A | 12/1996 | Weng et al. | |
| 5,605,155 A * | 2/1997 | Chalana et al. | 600/443 |
| 5,622,176 A | 4/1997 | Vintzileos et al. | |
| 5,740,266 A | 4/1998 | Weiss et al. | |
| 5,782,766 A * | 7/1998 | Weng et al. | 600/443 |
| 5,898,797 A | 4/1999 | Weiss et al. | |
| 6,048,314 A | 4/2000 | Nikom | |

(Continued)

FOREIGN PATENT DOCUMENTS

WO     WO 94/14132 A1     6/1994

OTHER PUBLICATIONS

Jeffery, Nathan, "Ossification and Midline Shape Changes of the Human Fetal Cranial Base", American Journal of Physical Anthropology 123:78-90, Wiley-Liss, Inc., 2004.

(Continued)

*Primary Examiner*—Francis J. Jaworski
(74) *Attorney, Agent, or Firm*—Daniel P. Burke & Associates, PLLC

(57) ABSTRACT

A method and system for assessing fetal abnormality based on landmarks. According to one embodiment, at least two coordinates are received for each of a plurality of points identifying a configuration of landmarks in a fetal image, and any of the received coordinates of any of the plurality of points are utilized as markers to assess fetal abnormality. According to another embodiment, at least two coordinates are received for each of a plurality of points identifying a configuration of landmarks in a fetal image, and one or more values resulting from a linear combination of any of the received coordinates of any of the plurality of points are utilized as markers to assess fetal abnormality.

39 Claims, 6 Drawing Sheets

U.S. PATENT DOCUMENTS

| | | | |
|---|---|---|---|
| 6,102,861 A * | 8/2000 | Avila et al. | 600/443 |
| 6,306,089 B1 | 10/2001 | Coleman et al. | |
| 6,585,647 B1 | 7/2003 | Winder | |
| 6,669,653 B2 * | 12/2003 | Paltieli | 600/588 |
| 6,695,780 B1 | 2/2004 | Nahum et al. | |
| 7,244,233 B2 * | 7/2007 | Krantz et al. | 600/443 |
| 2002/0133075 A1 | 9/2002 | Abdelhak | |

OTHER PUBLICATIONS

Kanokwan Tangchaitrong et al., "Fourier Anaylsis of Facial Profiles of Young Twins", American Journal of Physical Anthropology 113, 2000, pp. 369-379.

Pete E. Lestrel et al., "Fourier Analysis of the Cranium in Trisomy 21", Aug. 10, 1976, pp. 385-398.

Help Screen from NTSYSPC, Version 2.1, Fourier Analysis, no date.

Annabelle Azancot, M.D., et al., "Analysis of Ventricular Shape by Echocardiography in normal fetus, newborns and infants" vol. 68, No. 6, Dec. 1983, pp. 1201-1211.

Irwin R. Merkatz, M.D., et al., "An association between low material serum α-fetoprotein and fetal chromosomal abnormalities", vol. 148, No. 7, Apr. 1, 1984, pp. 886-894.

C. Lockwood, M.D., et al., "A sonographic screening method for Down Syndrome", Oct. 1987, pp. 803-808.

Michiel C. Van den Hof, M.D., et al., Evaluation of the lemon and banana signs in one hundred thirty fetuses with open Spina Bifida, vol. 162, No. 2, Feb. 1990, pp. 322-327.

J. E. Allanson, et al., "Anthropometric Craniofacial Pattern Profiles in Down Syndrome", 1993, Wiley-Liss, Inc., American Journal of Medical Genetics 47, pp. 748-752.

Noelle Stempfle, et al., "Skeletal abnormalities in fetuses with Down's Syndrome: A radiographic Post-Mortem Study", Pediatric Radiol,1999, pp. 682-687.

George Stetten, et al. "Real-Time Three-Dimensional Ultrasound Methods for Shape Analysis and Visualization", 2001, pp. 221-230.

Leslie G. Farkas, M.D., "Surface Anatomy of the Face in Down's Syndrome: Age-Related Changes of Anthropometric Proportion Indices in the Craniofacial Regions", The Journal of Craniofacial Surgery, vol. 13, No. 3, May 2002, pp. 368-374.

* cited by examiner

SYSTEM AND METHOD FOR ASSESSING FETAL ABNORMALITY BASED ON LANDMARKS

CROSS REFERENCE TO RELATED APPLICATIONS

This application claims the benefit under 35 U.S.C. § 119(e) of U.S. Provisional Application No. 60/490,540, filed Jul. 29, 2003 and U.S. Provisional Application No. 60/493,442, filed Aug. 8, 2003, both of which are hereby incorporated by reference as if repeated herein in their entirety.

BACKGROUND OF THE INVENTION

Prenatal screening methods are routinely employed to assess the likelihood of fetal abnormalities, commonly referred to as birth defects. For example, Down syndrome or Trisomy 21 is the most common cause of severe learning disability and accounts for approximately one half of all chromosomal anomalies in live born children.

Current methods to screen prenatally for trisomy 21 involve maternal serum testing for biochemical markers and/or ultrasound evaluation of biophysical markers. Maternal serum screening involves the quantitative analysis of biochemical markers and risk assessment based on likelihood ratios derived from the population distributions of affected and unaffected pregnancies. Ultrasound evaluation, however, has historically involved visual observation of a fetal image and deciding empirically whether the image looks "normal" or "abnormal" (for example, whether the cerebellum appears as a banana sign for open spina bifida). This approach requires extensive experience in the "art" of ultrasound and the interpretation is necessarily subjective.

Accordingly, there is a need in the art for a system and method that adequately evaluates the morphological changes observed with birth defects during prenatal screening.

SUMMARY OF THE INVENTION

Embodiments of the present invention provide for assessing fetal abnormality based on landmarks. According to one embodiment, at least two coordinates are received for each of a plurality of points identifying a configuration of landmarks in a fetal image, and any of the received coordinates of any of the plurality of points are utilized as markers to assess fetal abnormality. According to another embodiment, at least two coordinates are received for each of a plurality of points identifying a configuration of landmarks in a fetal image, and one or more values resulting from a linear combination of any of the received coordinates of any of the plurality of points are utilized as markers to assess fetal abnormality.

DETAILED DESCRIPTION

OVERVIEW

The use of multidimensional coordinates (Cartesian, polar, etc.) allows for the evaluation of each landmark in a configuration of landmarks against all of the other landmarks in the configuration. Landmark-based analysis of images begins with a set of two (or more) dimensional coordinates of distinct landmarks. Landmarks represent distinct anatomical features, for example, the chin, tip of nose, crown, rump, etc. They may also represent positions on a structure that are mathematically derived, for example a landmark may be place half-way along the edge of a bone. Fetal abnormalities identifiable through the use of the present invention may include, among others, Down syndrome, Spina Bifida, Trisomy 18, Trisomy 13, unbalanced translocation, other chromosomal abnormalities, heart abnormalities and abnormalities of any major body organ, structural abnormalities and craniofacial abnormalities.

Figure 1:
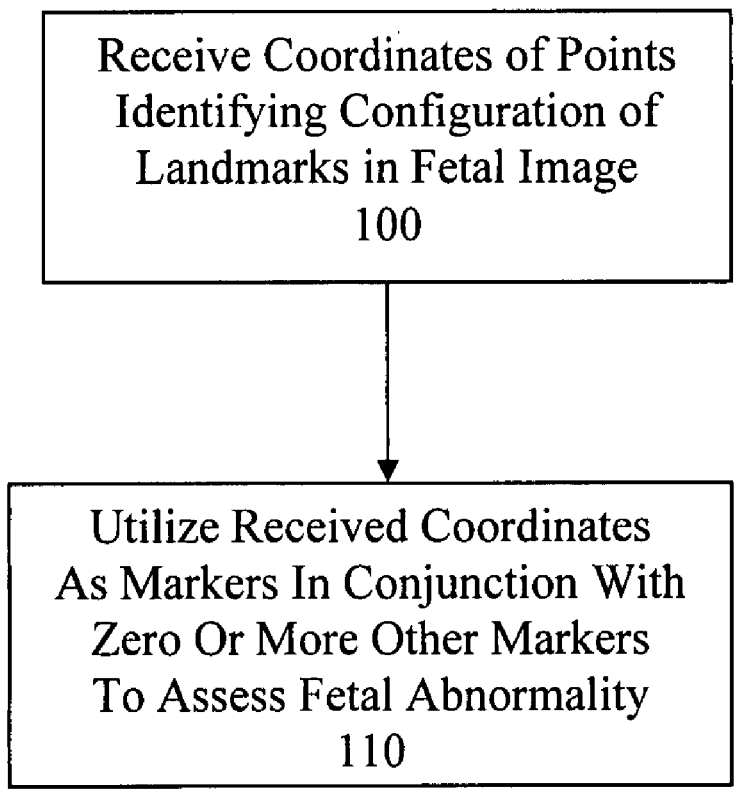
FIG. 1 is a flow chart that depicts a process for assessing fetal abnormality based on landmarks in accordance with an embodiment of the present invention.

FIG. 1 depicts a process for assessing fetal abnormality based on landmarks in accordance with an embodiment of the present invention. Upon receiving coordinates of points identifying a configuration of landmarks in a fetal image (step 100), the coordinates are used by themselves or with other markers as markers to assess fetal abnormality (step 110). A fetal abnormality may be assessed by comparing any of the received coordinates of any of the plurality of points to reference data of such markers by conducting a statistical analysis, such as a means calculation, a standard deviation calculation and/or a correlation calculation. The reference data may contain unaffected patients and/or affected patients. The statistical comparison could result in a risk of fetal abnormality, a likelihood ratio for a fetal abnormality or an index value that could be considered within range or outside of range for a fetal abnormality.

Figure 2:
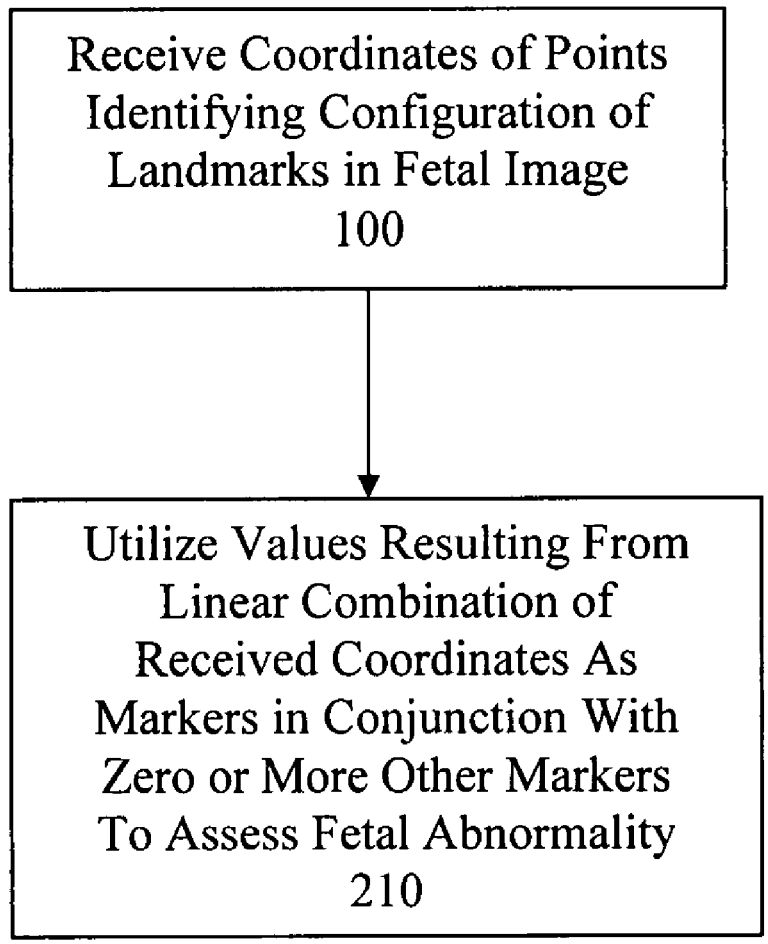
FIG. 2 is a flow chart that depicts a process for assessing fetal abnormality based on landmarks in accordance with an embodiment of the present invention.

FIG. 2 depicts another process for assessing fetal abnormality based on landmarks in accordance with an embodiment of the present invention. Upon receiving coordinates of points identifying a configuration of landmarks in a fetal image (step 200), values resulting from a linear combination of the coordinates are used by themselves or with other markers as markers to assess fetal abnormality (step 210). A fetal abnormality may be assessed by comparing one or more values resulting from a linear combination of any of the received coordinates of any of the plurality of points to reference data of such markers by conducting a statistical analysis, such as a means calculation, a standard deviation calculation and/or a correlation calculation. Again, the reference data may contain unaffected patients and/or affected patients, and the statistical comparison could result in a risk of fetal abnormality, a likelihood ratio for a fetal abnormality or an index value that could be considered within range or outside of range for a fetal abnormality.

According to embodiments of the present invention, a statistical landmark-based analysis involves the alignment of coordinate values of a particular configuration of points to a reference configuration and then the use of the aligned coordinate values, or of one or more linear combinations of the aligned coordinate values, as markers for a fetal abnormality. A marker is a quantity that can be used in statistical calculations to determine the likelihood of a patient carrying a fetus with a fetal abnormality. As part of the statistical calculations, the marker may be adjusted for other factors associated with the pregnancy such as gestational age or maternal weight. In addition, a mathematical transformation of the marker (e.g., the logarithm of the value of the marker or the square root of the value of the marker) is sometimes used in the statistical calculations. Furthermore, free Beta hCG, PAPP-A, nuchal translucency, AFP, intact hCG, unconjugated estriol, and inhibin are known markers for Down syndrome. The likelihood that a patient's pregnancy is associated with Down syndrome could be determined using one or more of these known markers and the coordinate markers.

Examples of other known markers include Ductus Venosus, absent or hypoplastic nasal bone observed on ultrasound, maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG, maternal blood hyperglycosylated hCG, ultrasound "soft markers" which include for example, nuchal edema or increased nuchal fold, short femur, hyperechogenic bowel, and echogenic foci in the heart, etc.

Architecture

Figure 3:
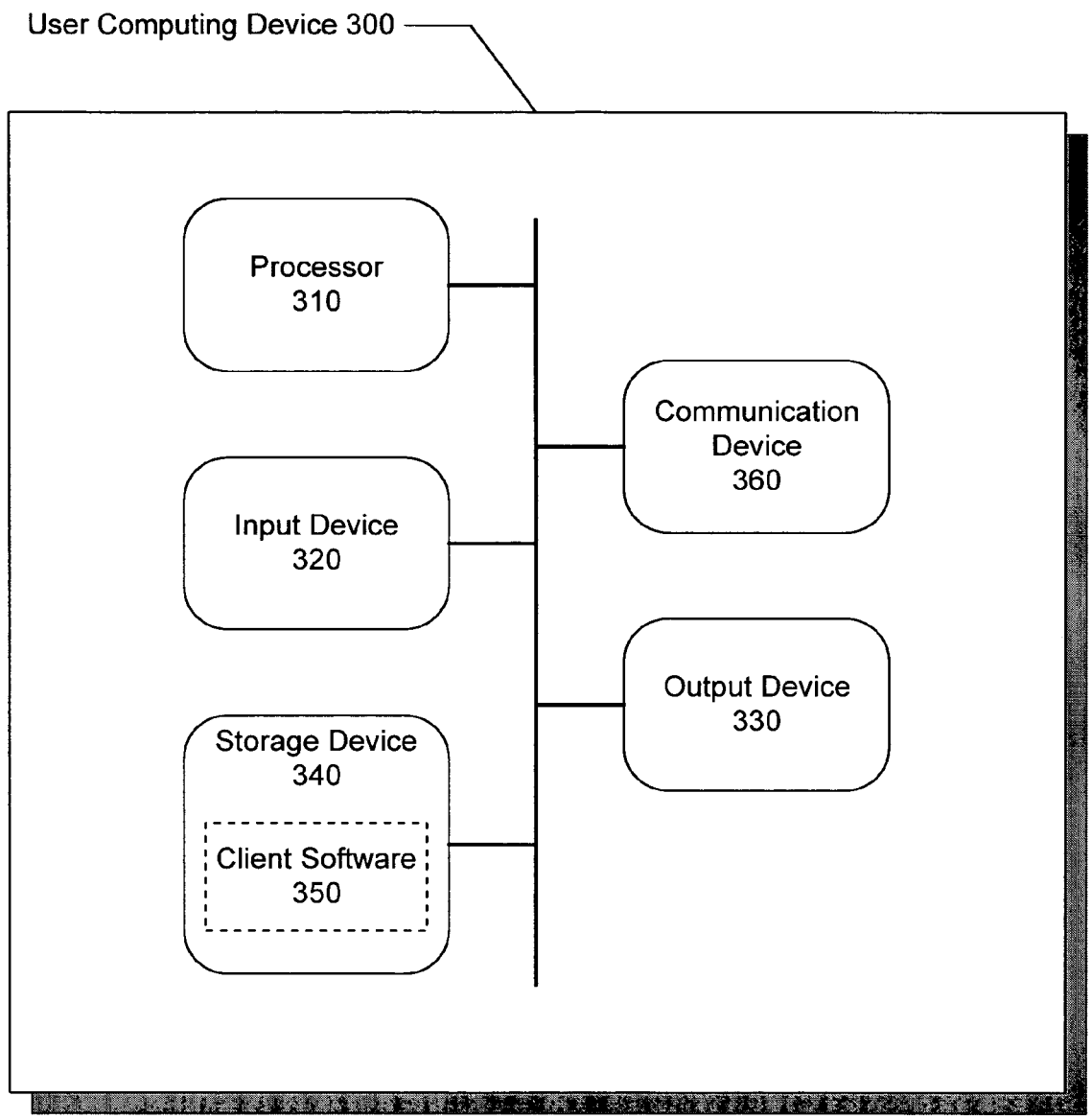
FIG. 3 is a block diagram that depicts a user computing device in accordance with an embodiment of the present invention.
Figure 4:
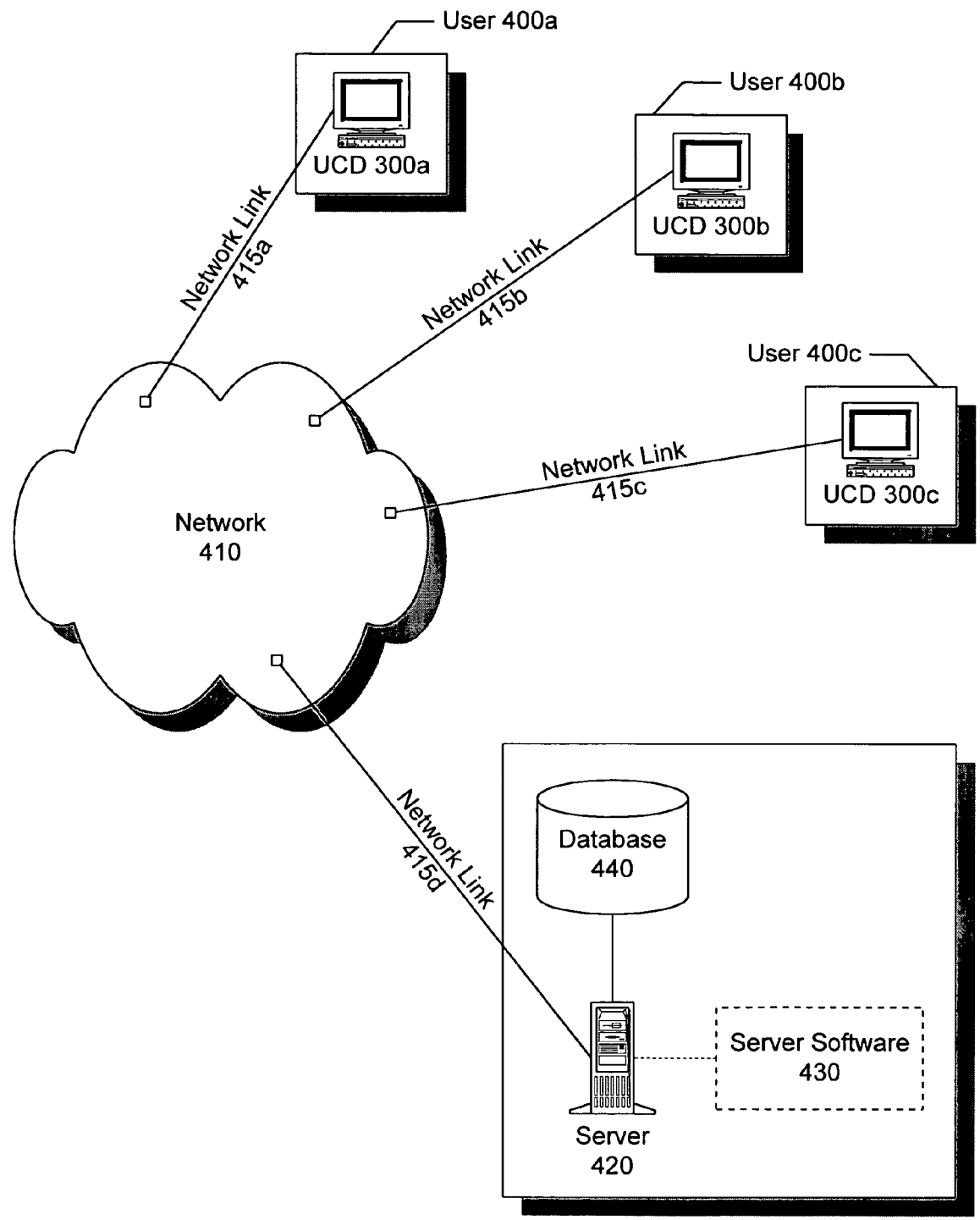
FIG. 4 is a block diagram that depicts a network architecture in accordance with an embodiment of the present invention.

FIGS. 3 and 4 illustrate the components of a basic computer and network architecture in accordance with an embodiment of the present invention. FIG. 3 depicts user computing device 300, which may be an ultrasound machine (3-D, 4-D or color), MRI or CAT scan machine, fetoscopy machine, workstation, personal computer, handheld personal digital assistant ("PDA"), or any other type of microprocessor-based device. User computing device 300 may include a processor 310, input device 320, output device 330, storage device 340, client software 350, and communication device 360.

Input device 320 may include a keyboard, mouse, pen-operated touch screen or monitor, voice-recognition device, or any other device that accepts input. Output device 330 may include a monitor, printer, disk drive, speakers, or any other device that provides output.

Storage device 340 may include volatile and nonvolatile data storage, including one or more electrical, magnetic or optical memories such as a RAM, cache, hard drive, CD-ROM drive, tape drive or removable storage disk. Communication device 360 may include a modem, network interface card, or any other device capable of transmitting and receiving signals over a network. The components of user computing device 300 may be connected via an electrical bus or wirelessly.

Client software 350 may be stored in storage device 340 and executed by processor 310, and may include, for example, imaging and analysis software that embodies the functionality of the present invention.

FIG. 4 illustrates a network architecture in accordance with an embodiment of the present invention. The network architecture allows the imaging and analysis functionality of the present invention to be implemented on more than one user computing device 300. For example, in one embodiment user computing device 300 may be an ultrasound machine that performs all of the imaging and analysis functionality of the present invention. In another embodiment, user computing device 300a may be an ultrasound machine that performs the imaging functionality of the present invention, and then transfers image or coordinate data over network 410 to server 420 or user computing device 300b or 300c for analysis of the data. The analyzed data could further be transferred to another user computing device 300 belonging to the patient or another medical services provider for testing with others markers.

Network link 415 may include telephone lines, DSL, cable networks, T1 or T3 lines, wireless network connections, or any other arrangement that implements the transmission and reception of network signals. Network 410 may include any type of interconnected communication system, and may implement any communications protocol, which may secured by any security protocol.

Server 420 includes a processor and memory for executing program instructions, as well as a network interface, and may include a collection of servers. In one particular embodiment, server 420 may include a combination of servers such as an application server and a database server. Database 440 may represent a relational or object database, and may be accessed via server 420.

User computing device 300 and server 420 may implement any operating system, such as Windows or UNIX. Client software 350 and server software 430 may be written in any programming language, such as ABAP, C, C++, Java or Visual Basic.

Landmark-Based Analysis

According to an embodiment of the present invention, coordinate data may be obtained from a set of at least three discrete landmarks on an image of a fetus using ultrasound or some other imaging technique. Coordinate data may be represented by a set of k values for each landmark where k is the number of dimensions. For example, in two dimensions, a landmark may be represented by the coordinates (2.8,0.9) indicating that the landmark is a distance of 2.8 from the origin in the x direction (horizontally) and a distance of 0.9 from the origin in the y direction (vertically). The first value (2.8) is often referred to as the x-coordinate and the second value is often referred to as the y-coordinate. In 3 dimensions, a third value is included and is often referred to as the z-coordinate.

The coordinate data may be aligned so that the image for any particular patient may be shifted (translated) or rotated compared to the coordinate data from other patients, but this shift or rotation would not represent a change in shape. In addition, as part of the alignment process the landmark configuration may be adjusted for size. In such a case the size of the configuration can be evaluated as a separate variable in any statistical analysis.

Having accounted for the effect of translation, rotation and/or size (scale), the aligned coordinates may then be utilized as markers for a fetal abnormality. If any coordinate points are fixed by the alignment process, these coordinate variables may be excluded. In a particular embodiment, the aligned coordinates may be utilized as markers by using one or more linear combinations of the aligned coordinate data, with each linear combination being a random variable in a statistical comparison with a reference set. A linear combination comprises a summation of two or more of the coordinate variables times a coefficient for each of the variables. A constant term may also be included in the linear combination. For example, a linear combination may consist of a weighted sum of all the X coordinates, a weighted sum of all the Y coordinates or a weighted sum of all of the coordinates.

Using the coordinate markers described above a statistical calculation may be performed by comparing the observed values of the coordinate markers in a particular ultrasound examination along with the observed values of other known markers to statistical parameters in a reference data set. The statistical parameters may include means, medians, percentiles, standard deviations, covariances, correlations or other known statistical parameters. These statistical parameters may be determined for a set of patients carrying unaffected fetuses and for a set of patients carrying a fetus affected with Down syndrome or other fetal abnormality. As part of the statistical analysis the coordinate markers may be adjusted for other factors related to the pregnancy. For example, the mean of a coordinate marker may be different at different gestational ages. Therefore, the coordinate marker may be adjusted for gestational age to account for this effect. An adjustment for gestational age is often used for markers in screening for Down syndrome.

One such method of comparison is the Mahalanobis Squared Distance which incorporates the mean and variance of each marker and the covariance between each pair of markers in a reference data set (usually of unaffected patients). A large MSD value would indicate an unusual configuration of the landmarks for the given fetus. Another such method of comparison is to calculate a likelihood ratio. A likelihood ratio is determined by dividing the relative frequency of the random variables in the affected distribution by the relative frequency in the unaffected distribution. The relative frequency can be determined based on a probability density function such as the multivariate Gaussian distribution function or other known distribution functions. A high likelihood ratio would indicate that the patient is at significantly greater risk of an abnormality after evaluating the configuration of the landmarks than before the evaluation took place. The likelihood ratio could be used to multiply a patient's a priori risk of fetal abnormality to determine a patient's posterior risk of fetal abnormality. A patient with a high posterior risk of a fetal abnormality may decide to have further diagnostic testing. As part of the process, a cut-off can be determined. For example, if a cut-off risk of 1 in 270 is used, patients with a final risk of 1 in 270 or greater would be considered screen positive and be counseled to have further testing while those with risks less than the cutoff would be considered screen negative and not be offered further diagnostic testing.

Alignment of Coordinate Data

There are several ways in which coordinate data could be aligned. Two common methods of alignment are two point registration and superimposition.

In the two point registration method, two landmarks are chosen for each configuration as the registration points. The coordinate data is then translated so that the first point always lies at (0,0). The configuration is then rotated so that the second point lies on the horizontal axis. Finally, the coordinate values are divided by the length of the distance between the first and second registration point, resulting in the second registration point falling at (1,0). The formula (using Matrix notation) for calculating the aligned coordinates of each point is as follows:

$$\begin{bmatrix} Vx \\ Vy \end{bmatrix} = \frac{1}{d}\begin{bmatrix} \cos\theta & \sin\theta \\ -\sin\theta & \cos\theta \end{bmatrix}$$ FORMULA A $d=\operatorname{sqrt}((Xb-Xa)^2+(Yb-Ya)^2)$, $\cos\Theta=(Xb-Xa)/d$ and $\sin\Theta=(Yb-Ya)/d$   FORMULAS B Xa, Ya represent the coordinates of the first registration point, Xb, Yb represent the coordinates of the second registration point, Xc,Yc represent the coordinates of any other point in the configuration and Vx and Vy represent the coordinates of the any other point after alignment. FORMULA B is calculated for each point in the configuration. At the conclusion of the alignment of a configuration with p landmarks, the transformed coordinates contain two fixed points, one at (0,0) and one at (1,0) and p-2 other x,y transformed coordinate pairs. The coordinate data from the two fixed points will be the same for every patient and thus are not utilized as markers for a fetal abnormality and can be excluded from further analysis. The data from the p-2 other x,y transformed coordinate pairs represent observed values of 2p-4 markers. If the configuration being evaluated is part of the reference data, one or more of these values could be used along with the values from other configurations in the reference dataset to determine statistical parameters for the one or more coordinate markers. If the configuration is being evaluated to determine a patient's risk of a fetal abnormality, then one or more of the 2p-4 values can be used to conduct a statistical comparison to the statistical parameters in the reference data set.

A second alternative for aligning the coordinate data is to superimpose the observed configuration to a reference configuration. A generalized least squares algorithm can be used to minimize the sum of the distances between each landmark in the observed configuration and each landmark in the reference configuration. The observed configuration and the reference configuration is centered and scaled. A configuration may be centered by subtracting the average of the x coordinates of all the landmarks in the configuration from each x coordinate value and subtracting the average of the y coordinates of all the landmarks in the configuration from each y coordinate value. A configuration may be scaled to centroid size 1 by first determining the centroid size (Square Root of the sum of the distances of each landmark from the center of the configuration) and then dividing each of the x and y coordinate values (after centering) for all of the landmarks by the centroid size. Then, the observed configuration is rotated to minimize the sum of the squared differences between corresponding coordinates in the observed configuration and the reference configuration. The last step is accomplished with the following formulas after both the observed configuration and the reference configuration are centered and scaled:

$\operatorname{Sum1}=\Sigma\ X_i{}^*X_{Ri}+Y_i{}^*Y_{Ri}$ $\operatorname{Sum2}=\Sigma\ X_i{}^*Y_{Ri}-Y_i{}^*X_{Ri}$ $\operatorname{New}X_i=X_i{}^*\operatorname{Sum1}-Y_i{}^*\operatorname{Sum2}$ $\operatorname{New}Y_i=X_i{}^*\operatorname{Sum2}+Y_i{}^*\operatorname{Sum1}$   FORMULAS C Where Xi and Yi are the landmark coordinates in the observed configuration, $X_{Ri}$ and $Y_{Ri}$ are the landmark coordinates in the reference configuration, and NewXi and NewYi are the landmark coordinates in the aligned configuration. After alignment, the centroid size of the aligned observed configuration may no longer be 1 so it can be rescaled to centroid size 1 by dividing each coordinate by the centroid size.

Reference Configuration

To determine the reference configuration, a set of configurations from a group of patients is first evaluated. Initially, one of the configurations may be designated as the reference configuration and is centered and scaled to centroid size one as described above. Alternatively, a consensus configuration can be determined and used as the reference configuration. To determine the consensus configuration, each of the configurations is aligned to one of the configurations being evaluated as described above. After the alignment, a new reference is determined by taking the average of the landmark values in each of the configurations at each of the landmarks. Each configuration is then aligned against the new reference configuration. The process is repeated until the reference configuration changes by less than a predetermined tolerance limit when compared to the previous reference. The software program TPSRELW can generate a reference configuration (called a consensus configuration) from a set of configurations of landmark coordinates.

Reference Data

As explained above, a statistical comparison may be made between the aligned coordinate data from an observed configuration and statistical parameters from a reference data set. Statistical parameters from the reference data set can be determined from the aligned coordinate data that was used to determine the reference configuration if a superimposition alignment is performed. However, once the reference configuration is determined, then configurations from another dataset could be aligned with the reference configuration and statistical parameters could be determined in part or totally from this data set.

In some statistical comparisons such as in the development of likelihood ratios, an observed configuration is compared to statistical parameters from more than one population such as the unaffected population and the population who may be carrying a fetus affected with a fetal abnormality. For example, when calculating a likelihood ratio the relative frequency for the unaffected population and the relative frequency for the affected population are determined. To accomplish this, observed data is compared to statistical parameters from the unaffected population and statistical parameters from the affected population. In such a case it is common to use one reference configuration and develop statistical parameters based on the aligned coordinates for each population. Then for each patient, the observed coordinates are aligned with the one reference configuration, and a relative frequency for the unaffected population and the affected population can be determined. Alternatively, a reference configuration for each population could be determined. Coordinates could be aligned with the reference configuration for each population and statistical parameters determined from the aligned coordinates for each population. The observed coordinates would then be aligned with each reference configuration, and a relative frequency based on the statistical parameters based on the aligned coordinates with each reference configuration could be determined for each population.

Instead of developing statistical parameters and making statistical comparisons based on aligned coordinates, the aligned coordinates may be transformed into a series of one or more linear combinations of the aligned coordinates. A description of various ways of transforming the aligned coordinates to linear combinations of aligned coordinates is discussed in a paper by F James Rohlf (Shape Statistics: Procrustes Superimpositions and Tangent Spaces. Journal of Classification 16:197-223). Some examples of linear combinations of aligned coordinates are principle component scores of procrustes tangent coordinates, Kendall tangent space coordinates and partial warp scores. The example embodiment below shows the use of a thin plate spline algorithm to determine a series of linear combinations of aligned coordinates, which can then be used as markers for Down syndrome.

EXAMPLE EMBODIMENT

Figure 5:
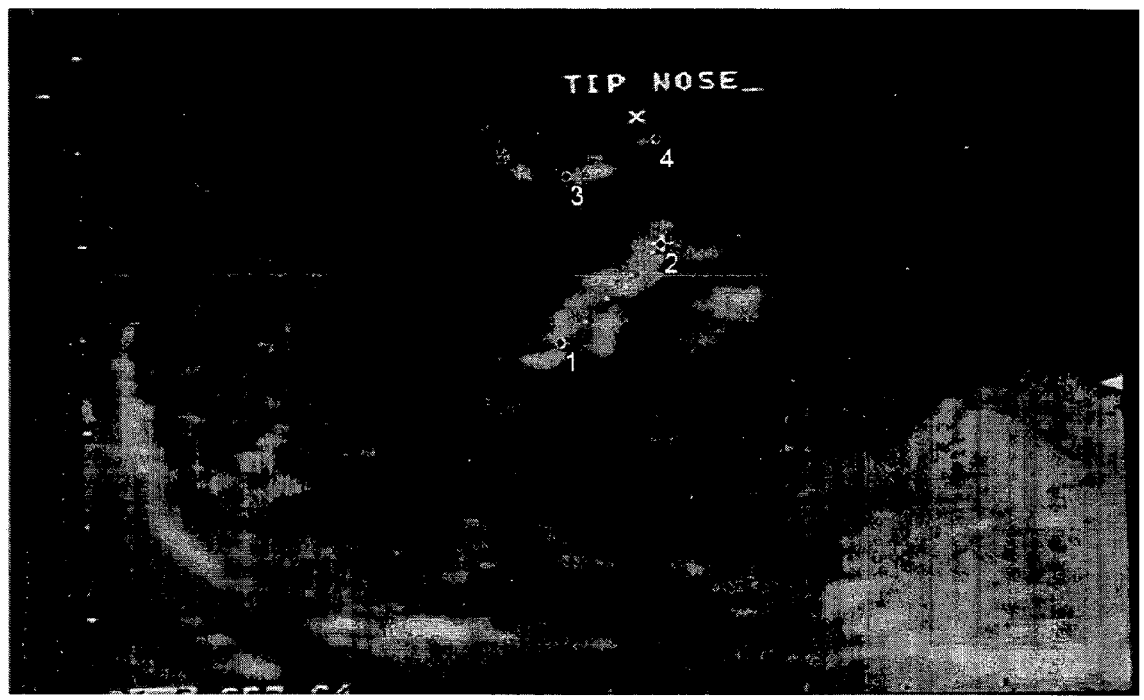
FIG. 5 is a screen shot that depicts selection of a configuration of landmarks in accordance with an embodiment of the present invention.

According to an embodiment of the present invention, ultrasound images of the sagittal view of the fetal face are collected to comprise a reference dataset for the assessment of the orientation of the maxilla to the nose. The images are oriented so that the fetus is facing up and the back of the head is towards the left. Images may be flipped horizontally to achieve the appropriate orientation if necessary. Four landmarks are selected on each image, as shown in FIG. 5 with respect to one particular image. The digitizing software TPSDIG may be used to obtain the coordinate values.

TABLE 1 lists the x and y coordinates for the four landmarks from nine images. X1 refers to the X coordinate of landmark1, Y1, refers to the Y coordinate of landmark 1, etc. Since the images will be adjusted for size in this example, the coordinate points are in pixels.

TABLE 1

| Image | X1 | X2 | X3 | X4 | Y1 | Y2 | Y3 | Y4 |
|---|---|---|---|---|---|---|---|---|
| 1 | 511 | 586 | 515 | 583 | 549 | 625 | 677 | 706 |
| 2 | 526 | 597 | 541 | 588 | 360 | 449 | 483 | 498 |
| 3 | 545 | 604 | 542 | 590 | 365 | 445 | 483 | 500 |
| 4 | 638 | 724 | 663 | 720 | 427 | 502 | 558 | 560 |
| 5 | 572 | 625 | 578 | 632 | 415 | 486 | 524 | 532 |
| 6 | 525 | 583 | 513 | 581 | 402 | 496 | 534 | 556 |
| 7 | 602 | 687 | 615 | 677 | 442 | 507 | 571 | 580 |
| 8 | 542 | 596 | 525 | 598 | 322 | 420 | 474 | 485 |
| 9 | 377 | 479 | 402 | 470 | 390 | 486 | 548 | 555 |

Next, another program called TPSRELW is used to align the images, obtain a reference configuration and create the aligned coordinates of each specimen to account for translation, rotation and size. The reference configuration is as follows:

| | X | Y |
|---|---|---|
| Landmark 1: | −0.27317 | −0.68546 |
| Landmark 2: | 0.26893 | −0.04845 |
| Landmark 3: | −0.22843 | 0.31585 |
| Landmark 4: | 0.23268 | 0.41806 |

TABLE 2 lists the aligned coordinates for each of the specimens rounded to the fourth decimal place after scaling the coordinates to have centroid size 1.

TABLE 2

| Image | X1 | X2 | X3 | X4 | Y1 | Y2 | Y3 | Y4 |
|---|---|---|---|---|---|---|---|---|
| 1 | −0.2714 | 0.2678 | −0.2426 | 0.2462 | −0.6487 | −0.1024 | 0.2714 | 0.4798 |
| 2 | −0.3053 | 0.2767 | −0.1773 | 0.2059 | −0.7102 | 0.0106 | 0.2899 | 0.4097 |
| 3 | −0.2803 | 0.2835 | −0.2119 | 0.2086 | −0.6857 | −0.0544 | 0.3171 | 0.4230 |
| 4 | −0.2820 | 0.2952 | −0.2213 | 0.2081 | −0.6886 | −0.0368 | 0.3272 | 0.3982 |
| 5 | −0.2583 | 0.2179 | −0.2308 | 0.2712 | −0.7010 | −0.0243 | 0.3182 | 0.4070 |
| 6 | −0.2645 | 0.2406 | −0.2493 | 0.2732 | −0.6855 | −0.0331 | 0.3045 | 0.4142 |
| 7 | −0.2699 | 0.3224 | −0.2543 | 0.2019 | −0.6456 | −0.1078 | 0.3236 | 0.4297 |
| 8 | −0.2308 | 0.2085 | −0.2444 | 0.2667 | −0.6963 | −0.0572 | 0.3637 | 0.3898 |
| 9 | −0.2886 | 0.3004 | −0.2178 | 0.2060 | −0.6889 | −0.0293 | 0.3185 | 0.3997 |

Where X1 refers to the X coordinate of landmark1, Y 1 refers to the Y coordinate of landmark 1, etc.

Next, a thin-plate spline algorithm is used as described in the book "Morphometric Tools for Landmark data: Geometry and Biology" by Bookstein F. L. (1991). The thin plate spline algorithm is often used to describe shape variation since it provides formulas for visualizing the difference between coordinate configurations using grids. As part of the thin plate spline algorithm, a series of vectors called non-uniform (principal warps) and uniform shape coefficients are determined. There are 2p-6 (where p=number of landmarks, in this case 4) non-uniform shape vectors and 2 uniform shape coefficient vectors for any configuration of points. At least four landmarks are used in order to determine non-uniform shape vectors.

TABLE 3 lists the principal component and uniform shape coefficient matrix which can be developed from the output of the TPSRELW program. The TPSRELW program provides the 4 non-zero coefficients which are shown in the table below in the first 2 columns and the 8 coefficients in the UniX and UniY columns.

TABLE 3

| PX1 | PY1 | UniX | UniY |
|---|---|---|---|
| 0.283069 | 0.000000 | 0.262521 | −0.243422 |
| −0.591377 | 0.000000 | 0.288121 | 0.494365 |
| −0.357030 | 0.000000 | −0.452322 | −0.516666 |
| 0.665338 | 0.000000 | −0.098320 | 0.265723 |
| 0.000000 | 0.283069 | 0.245433 | 0.252537 |
| 0.000000 | −0.591377 | −0.490875 | 0.289523 |
| 0.000000 | −0.357030 | 0.511624 | −0.450312 |
| 0.000000 | 0.665338 | −0.266182 | −0.091748 |

TABLE 3 can be used as a matrix to weight the aligned coefficients to define four markers which represent a series of linear combinations of the aligned coordinates.

The four coordinate markers are:

$PX1 = 0.283069*X1 - 0.591377*X2 - 0.357030*X3 + 0.665338*X4$ $PY1 = 0.283069*Y1 - 0.591377*Y2 - 0.357030*Y3 + 0.665338*Y4$ $UniX = 0.262521*X1 + 0.288121*X2 - 0.452322*X3 - 0.098320*X4 + 0.2454433*Y1 - 0.490875*Y2 + 0.511624*Y3 - 0.266182*Y4$ $UniY = -0.243422*X1 + 0.494365*X2 - 0.516666*X3 + 0.265723*X4 + 0.252537*Y1 + 0.289523*Y2 - 0.450312*Y3 - 0.091748*Y4$     FORMULAS D

Where X1, . . . ,X4,Y1, . . . ,Y4 represent the aligned coordinate values of the four landmarks. In some cases, the value of each linear combination can be determined for the reference configuration and then subtracted from each observed value for each of the markers (PX1, PY1, UniX, UniY). The resulting observed values after accounting for the subtraction are often referred to as partial warp scores.

TABLE 4 lists the observed values of the four markers for the nine patients in the reference dataset along with their mean and standard deviation.

TABLE 4

| Image | PX1 | PY1 | UniX | UniY |
|---|---|---|---|---|
| 1 | 0.01526 | 0.09929 | −0.00639 | 0.02949 |
| 2 | −0.04980 | −0.03820 | −0.08067 | 0.01299 |
| 3 | −0.03259 | 0.00632 | −0.00853 | 0.00278 |
| 4 | −0.03697 | −0.02506 | 0.00109 | 0.01580 |
| 5 | 0.06088 | −0.02688 | −0.03297 | −0.00275 |
| 6 | 0.05361 | −0.00762 | −0.02065 | 0.02693 |
| 7 | −0.04192 | 0.05138 | 0.06287 | 0.03072 |
| 8 | 0.07602 | −0.03380 | 0.02331 | −0.03557 |
| 9 | −0.04449 | −0.02543 | −0.00909 | 0.02348 |
| Mean | 0.00000 | 0.00000 | −0.00789 | 0.01154 |
| SD | 0.05152 | 0.04636 | 0.03898 | 0.02118 |

An atypicality index (AI) is developed to determine if an observed configuration of cooridnates is an outlier based on the four coordinate markers PX1, PY1, UniX and UniY:

$$AI = Z_{PX1}^2 + Z_{PY1}^2 + Z_{uniX}^2 + Z_{uniY}^2 \qquad \text{FORMULA E}$$

where Z=(Observed Value−Mean)/SD.

A value of 9.488, equal to the 95$^{th}$ percentile of a Chi-squared distribution with four degrees of freedom is set as a cut-off.

Figure 6:
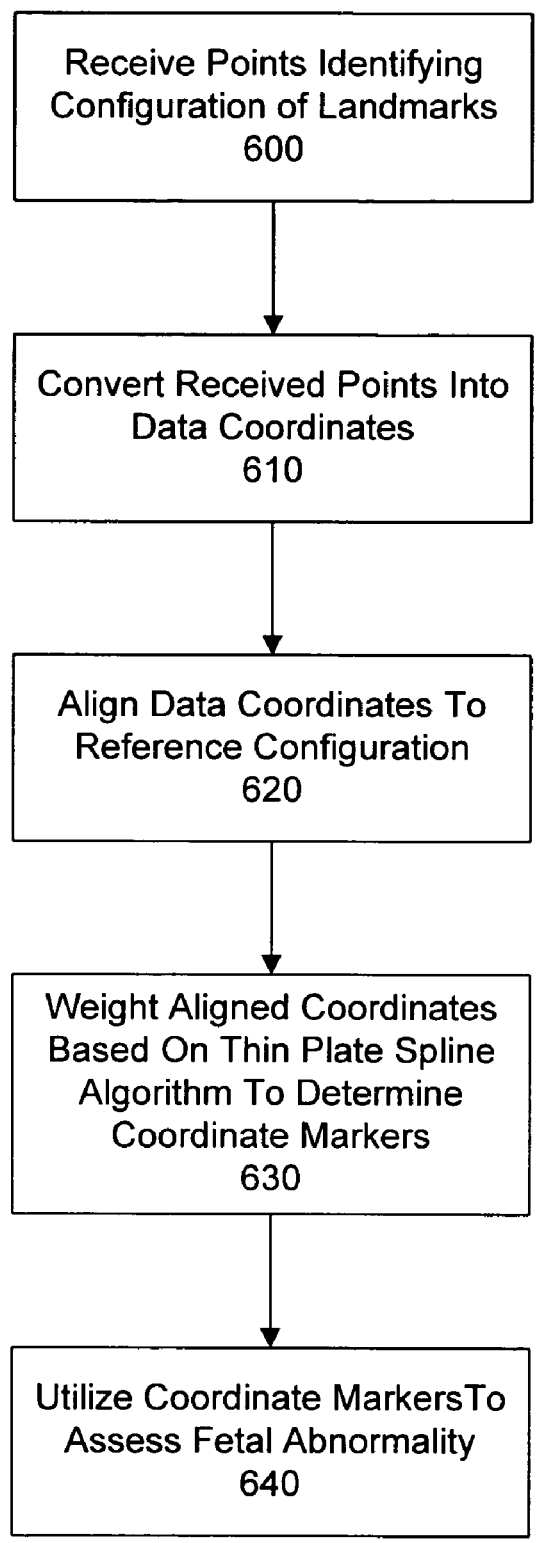
FIG. 6 is a flow chart that depicts a process for analyzing a configuration of landmarks on a fetal face image to determine risk of fetal abnormality in accordance with an embodiment of the present invention.

Thus, in accordance with the reference dataset described above, FIG. 6 provides an example embodiment of the present invention in which a configuration of landmarks is analyzed on fetal face image. A sagittal view of the fetal face is obtained by ultrasound (e.g., UCD 300a) to assess the orientation of the maxilla to the nose. In step 600, digitizing software (e.g., client software 350), such as TPSDIG, DigitX, CalExcel, DSDigit, Digical, Windig or MacMorph, is employed by a user (e.g., user 400b) to receive points identifying the configuration of the four landmarks to be analyzed, as shown in FIG. 5. (Digitizing software provides coordinate data when a user clicks on a particular point in a bit-map image.)

In step 610, the user-identified landmark configuration points are converted into data coordinates by the digitizing software as follows:

| X1 | X2 | X3 | X4 | Y1 | Y2 | Y3 | Y4 |
|---|---|---|---|---|---|---|---|
| 527 | 584 | 531 | 581 | 482 | 535 | 578 | 597 |

In step 620, the coordinates of this configuration are then centered and scaled to size 1, and then aligned with the reference configuration using FORMULAS C. The aligned coordinates after re-scaling to centroid size 1 are as follows:

| X1 | X2 | X3 | X4 | Y1 | Y2 | Y3 | Y4 |
|---|---|---|---|---|---|---|---|
| −0.2655 | 0.2755 | −0.2448 | 0.2349 | −0.6433 | −0.1203 | 0.2853 | 0.4783 |

In step 630, the coordinates are weighted based on a thin plate spline algorithm by using FORMULAS D. The observed values of the four coordinate markers PX1, PY1, UniX and UniY are:

| PX1 | PY1 | UniX | UniY |
|---|---|---|---|
| 0.00561 | 0.10546 | 0.01717 | 0.02006 |

In step 640, the coordinate markers are utilized to assess fetal abnormality by the calculation of the atypicality index of 5.7611 (using FORMULA E). This particular AI is below the cut-off indicating that this patient is not at increased risk for a fetal abnormality.

Several embodiments of the invention are specifically illustrated and/or described herein. However, it will be appreciated that modifications and variations of the invention are covered by the above teachings and within the purview of the appended claims without departing from the spirit and intended scope of the invention.

What is claimed is:

1. A computer-implemented method for assessing a fetal abnormality selected from the group consisting of chromosomal abnormalities and fetal structural abnormalities based on landmarks, comprising:
    establishing a method of alignment for observed coordinates and reference coordinates;
    providing a reference data set of at least three predetermined discrete landmarks, said reference data set comprising aligned coordinates of affected and unaffected fetuses;
    receiving at least two coordinates for each of at least three points identifying a configuration of landmarks in a fetal image;
    aligning said received coordinates using said alignment method; and
    utilizing said aligned received coordinates of said at least three points and said aligned reference coordinates as markers to assess the likelihood of a fetal abnormality in a fetus from which said received coordinates were obtained.

2. The method of claim 1, wherein the fetal abnormality is a chromosomal abnormality.

3. The method of claim 2, wherein the chromosomal abnormality is Down syndrome.

4. The method of claim 1, wherein the fetal abnormality is Spina Bifida.

5. The method of claim 1, wherein the points are selected by a user on a computer monitor.

6. The method of claim 1, wherein the points are selected on a 3D ultrasound image displayed on a computer monitor.

7. The method of claim 1, wherein said step of receiving coordinates comprises receiving coordinates for more than 3 points.

8. The method of claim 1, wherein the received coordinates are aligned to a reference configuration of landmarks.

9. The method of claim 1, wherein the utilization of the received coordinates as markers comprises conducting a statistical analysis on the received coordinates to determine a likelihood of a patient carrying a fetus with a fetal abnormality.

10. The method of claim 9, wherein the statistical analysis includes a statistical comparison of the received coordinates with reference parameters derived from a statistical distribution of such markers in an unaffected population and/or affected population.

11. The method of claim 10, wherein the statistical comparison includes at least one of a means calculation, a standard deviation calculation and a correlation calculation.

12. The method of claim 10, wherein the statistical analysis results in an indication of risk of fetal abnormality.

13. The method of claim 10, wherein the statistical analysis results in a likelihood ratio for a fetal abnormality.

14. The method of claim 10, wherein the statistical analysis results in an index value to be considered within range or outside of range for a fetal abnormality.

15. The method of claim 1, comprising utilizing the received coordinates as markers in combination with one or more additional markers to assess fetal abnormality.

16. The method of claim 15, wherein the one or more additional markers includes at least one biochemical marker selected from the group consisting of free Beta hCG and PAPP-A, maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG and maternal blood hyperglycosylated hCG.

17. The method of claim 15, wherein the one or more additional markers includes at least one ultrasound marker selected from the group consisting of nuchal translucency, DuctusVenosus, absent or hypoplastic nasal bone, nuchal edema, short femur, hyperechogenic bowel and echogenic foci in the heart.

18. A machine-readable medium having stored thereon a plurality of executable instructions for assessing a fetal abnormality selected from the group consisting of chromosomal abnormalities and fetal structural abnormalities based on landmarks, the plurality of executable instructions comprising;
    establishing a method of alignment for observed coordinates and reference coordinates;

providing a reference data set of at least three predetermined discrete landmarks, said reference data set comprising aligned coordinates of affected and unaffected receiving at least two coordinates for each of at least three points identifying a configuration of landmarks in a fetal image;

aligning said received coordinates using said alignment method; and utilizing said aligned received coordinates of any of said at least three points and said aligned reference coordinates as markers to assess the likelihood of a fetal abnormality in a fetus from which said received coordinates were obtained.

19. A system for assessing a fetal abnormality selected from the group consisting of chromosomal abnormalities and fetal structural abnormalities based on landmarks, comprising:

means for aligning observed coordinates, providing a reference data set of at least three predetermined discrete landmarks, said reference data set comprising aligned coordinates of affected and unaffected fetuses, receiving at least two coordinates for at least three points identifying a configuration of landmarks in a fetal image; and means for aligning said received coordinates using said alignment method, and utilizing said aligned received coordinates of said at least three points and said aligned reference coordinates as markers to assess the likelihood of a fetal abnormality in a fetus from which said received coordinates were obtained.

20. A computer-implemented method for assessing a fetal abnormality selected from the group consisting of chromosomal abnormalities and fetal structural abnormalities based on landmarks, comprising;

establishing a method of alignment for observed coordinates and reference coordinates;

providing a reference data set of at least three predetermined discrete landmarks, said reference data set comprising aligned coordinates of affected and unaffected fetuses;

receiving at least two coordinates for each of at least three points identifying a configuration of landmarks in a fetal image;

aligning said received coordinates using said alignment method; and utilizing one or more values resulting from a linear combination of any of the received coordinates of any of the at least three points as markers and said aligned reference coordinates to assess the likelihood of a fetal abnormality.

21. The method of claim 20, wherein the fetal abnormality is a chromosomal abnormality.

22. The method of claim 21, wherein the chromosomal abnormality is Down syndrome.

23. The method of claim 20, wherein the fetal abnormality is Spina Bifida.

24. The method of claim 20, wherein the points are selected by a user on a computer monitor.

25. The method of claim 20, wherein the points are selected on a 3D ultrasound image displayed on a computer monitor.

26. The method of claim 20, wherein the configuration includes more than 3 landmarks.

27. The method of claim 20, wherein the received coordinates are aligned to a reference configuration of landmarks.

28. The method of claim 20, wherein the one or more values are based on a thin plate spline algorithm.

29. The method of claim 20, wherein the utilization of the one or more values as markers comprises conducting a statistical analysis on the one or more values to determine a likelihood of a patient carrying a fetus with a fetal abnormality.

30. The method of claim 29, wherein the statistical analysis includes a statistical comparison of the one or more values with reference parameters derived from a statistical distribution of such markers in an unaffected population and/or affected population.

31. The method of claim 30, wherein the statistical comparison includes at least one of a means calculation, a standard deviation calculation and a correlation calculation.

32. The method of claim 30, wherein the statistical analysis results in an indication of risk of fetal abnormality.

33. The method of claim 30, wherein the statistical analysis results in a likelihood ratio for a fetal abnormality.

34. The method of claim 30, wherein the statistical analysis results in an index value to be considered within range or outside of range for a fetal abnormality.

35. The method of claim 20, comprising utilizing the one or more values as markers in combination with one or more additional markers to assess fetal abnormality.

36. The method of claim 35, wherein the one or more additional markers includes at least one biochemical marker selected from the group consisting of free Beta hCG and PAPP-A, maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG and maternal blood hyperglycosylated hCG.

37. The method of claim 35, wherein the one or more additional markers includes at least one ultrasound marker selected from the group consisting of nuchal translucency, Ductus Venosus, absent or hypoplastic nasal bone, nuchal edema, short femur, hyperechogenic bowel and echogenic foci in the heart.

38. A machine-readable medium having stored thereon a plurality of executable instructions for assessing a fetal abnormality selected from the group consisting of chromosomal abnormalities and fetal structural abnormalities based on landmarks, the plurality of executable instructions comprising;

establishing a method of alignment for observed coordinates and reference coordinates:

providing a reference data set of at least three predetermined discrete landmarks, said reference data set comprising aligned coordinates of affected and unaffected receiving at least two coordinates for each of at least three points identifying a configuration of landmarks in a fetal image;

aligning said received coordinates using said alignment method; and utilizing one or more values resulting from a linear combination of any of the received coordinates of any of the at least three points as markers to assess the likelihood of a fetal abnormality.

39. A system for assessing a fetal abnormality selected from the group consisting of chromosomal abnormalities and fetal structural abnormalities based on landmarks, comprising:

means for establishing a method of alignment for observed coordinates and reference coordinates, providing a reference data set of at least three predetermined discrete landmarks, said reference data set comprising aligned coordinates of affected and unaffected fetuses; and, means for receiving at least two coordinates for each of at least three points identifying a configuration of landmarks in a fetal image, aligning said received coordinates using said alignment method, and utilizing one or more values resulting from a linear combination of any of the received coordinates of any of the plurality of points as markers to assess fetal abnormality.

* * * * *